United States Patent [19]
Perry

[11] Patent Number: 5,765,548
[45] Date of Patent: Jun. 16, 1998

[54] USE OF NITRIC OXIDE IN THE TREATMENT OF EXERCISED INDUCED PULMONARY HEMORRHAGING IN EQUINE

[76] Inventor: Bryan J. Perry, 479 Lydecker Rd., West Seneca, N.Y. 14224

[21] Appl. No.: 643,964

[22] Filed: May 7, 1996

[51] Int. Cl.$^6$ .................................................. A61M 15/00
[52] U.S. Cl. ............................. 128/200.24; 128/203.12; 128/205.22
[58] Field of Search .................... 128/203.12, 205.22, 128/200.24, 207.14

[56] References Cited

U.S. PATENT DOCUMENTS

| | | | |
|---|---|---|---|
| 5,062,423 | 11/1991 | Matson et al. | 128/207.15 |
| 5,396,882 | 3/1995 | Zapol | 128/200.14 |
| 5,485,827 | 1/1996 | Zapol et al. | 128/200.14 |
| 5,536,241 | 7/1996 | Zapol | 604/23 |
| 5,570,683 | 11/1996 | Zapol | 128/200.14 |

OTHER PUBLICATIONS

Pulmonary Artery Wedge Pressure Increases With High–Intensity Exercise In Horses; Murli Manobar, BVSc, PhD; pp. 142–146; Am J Vet Res, vol. 54 No. 1, Jan., 1993.

Stress Failure Of Pulmonary Capillaries in Racehorses With Exercise–Induced Pulmonary Hemorrhage; John B. West et al.; pp. 2–14; 1993 the American Physiological Society.

Ultrastructural Appearances Of Pulmonary Capillaries At High Transmural Pressures; Tsukimoto et al. pp. 4–13; 1991 American Physiological Society.

Fast Track Pulmonary Artery Pressure During Exercise In The Horse After Inhibition Of Nitric Oxide Synthase; Mills et al.; pp. 1–4; 1996 Bailliere Tindall.

*Primary Examiner*—Aaron J. Lewis
*Attorney, Agent, or Firm*—Hodgson, Russ, Andrews, Woods & Goodyear LLP

[57] ABSTRACT

The administration of nitric oxide in controlled doses to horses during high intensity exercise is described. The nitric oxide is beneficial to prevent exercised induced pulmonary hemorrhaging by reducing pulmonary artery pressure with a concomitant compensating reduction in pulmonary vascular resistance. The nitric oxide is either administered to the equine through inhalation during exercise or via a stand alone nitric oxide gas source followed by an intramuscular injection of a nitric oxide augmenter prior to exercise.

28 Claims, 2 Drawing Sheets

USE OF NITRIC OXIDE IN THE TREATMENT OF EXERCISED INDUCED PULMONARY HEMORRHAGING IN EQUINE

BACKGROUND OF INVENTION

1. Field of the Invention

The present invention generally relates to the pulmonary hemodynamics of equine, and more particularly to pulmonary hemorrhaging in equine. Still more particularly, the present invention relates to the prevention of exercised induced pulmonary hemorrhaging in performance horses.

2. Prior Art

Although numerous hypotheses have been advanced in recent years, it is generally suggested that capillary stress failure is a causal determinant of exercised induced pulmonary hemorrhaging (EIPH) in performance animals such as horses. This rationale is based on studies by M. Manohar (Am. J. Vet. Res., 1993, 54:142–146) and West et al. (J. Apple Physiol., 1991, 71:573–582 and J. Appl. Physiol., 1993, 75:1097–1109) who have demonstrated that increased high pulmonary artery pressure, pulmonary artery wedge pressure and stress failure at the capillary level are due to increased transmural pressure during strenuous exercise of equine. Further, it is known that the horse has a relatively thin pulmonary blood-gas barrier to facilitate oxygen uptake during high intensity exercise. During exercise, pulmonary blood flow increases by as much as eight fold to satisfy the increased oxygen need. The concurrent increase in pulmonary artery pressure is compensated for by a reduction in pulmonary vascular resistance and functional recruitment of the capillary bed.

Mills et al. (Br. Vet. J., 1996, 152:119–122) have studied the synthesis of nitric oxide (NO) in horses subjected to treadmill tests by introducing N-nitro-L-arginine methyl ester (L-NAME) directly into the pulmonary artery. This compound has been shown to inhibit the in situ production of NO which is known to regulate basal pulmonary vascular tone in many species. During exercise, a reduced level of NO in the lungs resulted in a significant increase in the pulmonary artery pressure. Contrastingly, the introduction of L-arginine, a structural analogue of L-NAME, into the pulmonary artery of exercised horses was shown by West et al. to reverse the restricted production of NO with a concomitant reduction in pulmonary artery pressure.

SUMMARY OF INVENTION

The present invention is premised on the occurrence of capillary stress failure resulting from excessively high transmural pulmonary artery pressure as the underlying mechanism leading to exercise induced pulmonary hemorrhaging in the equine. Capillary stress failure produces occult hemorrhaging into the lung/tracheobronchial tree, which may be clinical (obvious bleeding through nares and mouth) or sub-clinical (endoscopic scoring) in its presentation As a solution, the administration of nitric oxide in controlled doses to horses during high intensity exercise is beneficial to obtund pulmonary artery pressure with a concomitant compensating reduction in pulmonary vascular resistance. The nitric oxide is either administered to the equine through inhalation during exercise or via a stand alone nitric oxide gas source followed by an intramuscular injection of a nitric oxide augmenter prior to exercise.

The foregoing and additional advantages and characterizing features of the present inventions will become clearly apparent upon a reading of the ensuing detailed description together with the included drawings wherein:

DETAILED DESCRIPTION OF THE PREFERRED EMBODIMENTS

Nitric oxide (NO), previously known as endothelial derived relaxing factor, is a molecule that participates in the regulation of vascular tone. It is a selective pulmonary vasodilator and has been demonstrated to exhibit marked vasodilatory effects on the pulmonary circulation. Nitric oxide is an ideal local transcellular messenger because of its small size, lipophilic nature and short duration of action. In vascular endothelial cells, nitric oxide is synthesized from the terminal guanidine nitrogen of L-arginine and diffuses rapidly into subadjacent vascular smooth muscle. There, the nitric oxide binds to the heme iron complex of soluble quanylate cyclase. The resulting nitrosyl-heme activates quanylate cyclase, stimulating the production of cyclic 3',5'-monophosphate (cGMP) and subsequent relaxation of vascular smooth muscle. When nitric oxide diffuses into the intravascular space, its biological activity is limited by avid binding to hemoglobin. In order for the therapeutics to be effective, the nitric oxide needs to be continuously administered to the horse throughout the duration of the high intensity exercise.

Accordingly, cGMP needs to be produced throughout the duration of the physical exercise to maintain the vascular smooth muscle in a relaxed state to thereby prevent capillary stress failure. It is contemplated by the scope of the present invention that continuous production of cGMP is provided by inhalation of nitric oxide throughout the duration of the exercise and/or inhalation of nitric oxide followed by an intramuscular injection of a nitric oxide augmenter just before exercise.

Figure 1:
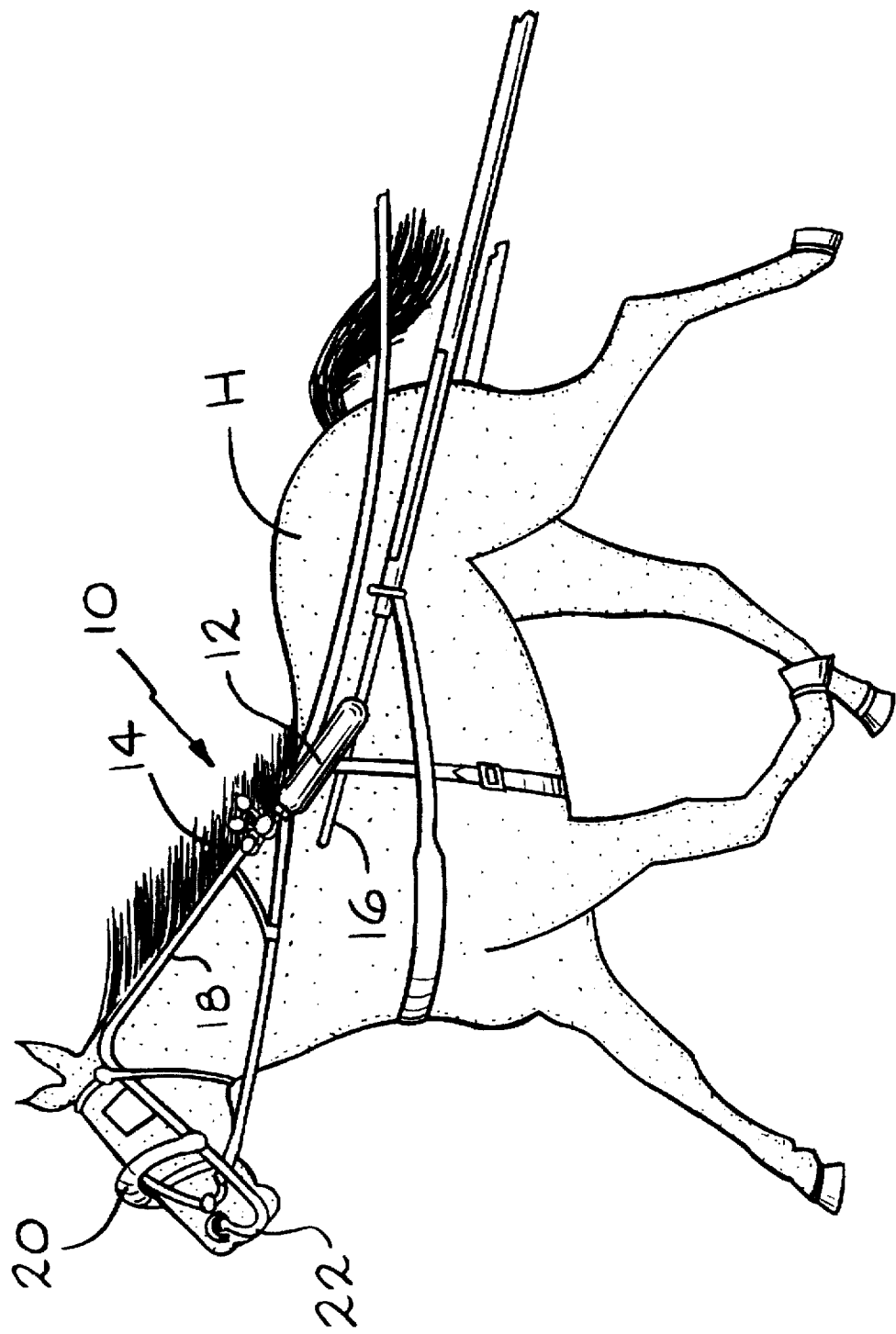
FIG. 1 is a perspective view of a horse H provided with a nitric oxide delivery system 10 according to the present invention.
Figure 2:
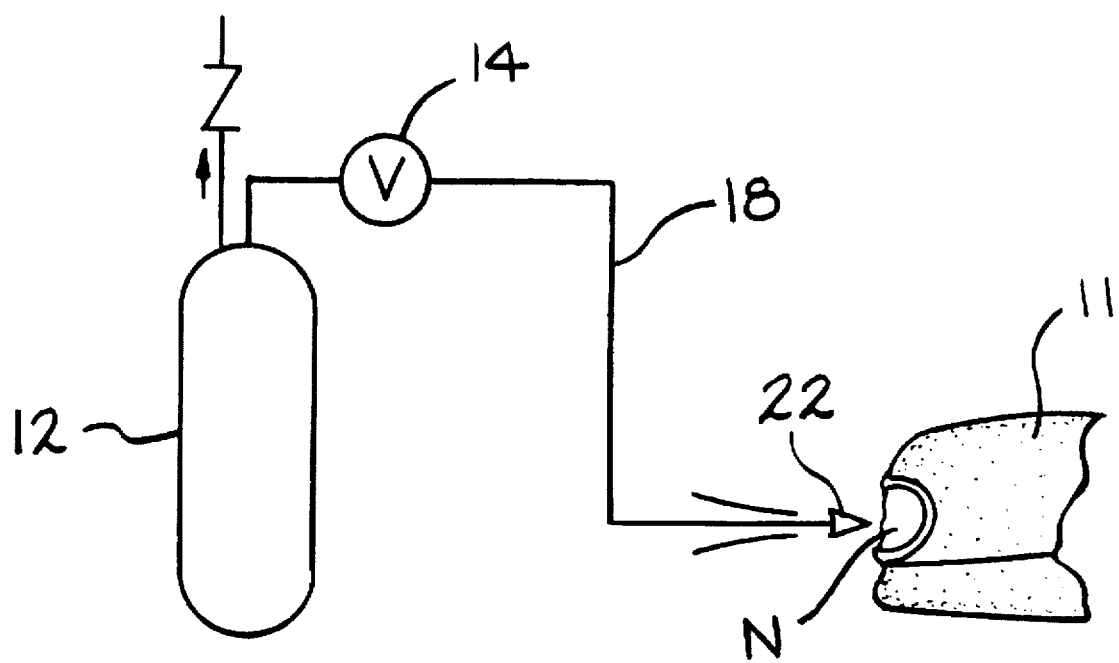
FIG. 2 is a partial schematic view of the present nitric oxide delivery system.

Turning now to the drawings, FIGS. 1 and 2 show a delivery system 10 for continuous nasal insufflation of nitric oxide to a horse H during high intensity exercise. The nitric oxide delivery system 10 includes a container 12 such as a P-1 nitric oxide (1000 ppm) $N_2$ gas cylinder having an on/off valve that is mated to a pressure regulator/flowmeter 14. The container 12 is preferably anchored to the tack of the horse H in an area near the rider, for example, proximate the saddle pads or sulky/training cart shaft 16. The single stage pressure regulator with associated flowmeter preferably quantifies the NO flow rate between 0 to 1 l/min. in increments of 100 ml/min.; 1 L/min. up to a maximum of 18 L/min. Such a pressure regulator/flowmeter is available under Model #3510-660 from Western Enterprises, West Lake, Ohio.

A flexible conduit 18, for example, 0.25 I.D. flexible polytetrafluoroethylene tubing connects to the pressure regulator 14 and traverses along the length of the dorsum of the neck and the bridle to the nose band (shadow roll) 20 of the bridle. There it connects to the proximal end of a rigid, half-round flanged exit port 22 which is also connected to the nose band. The distal end of the half-round exit port 22 is disposed proximate the horse's nares. Typically, only one flanged exit port 22 is required adjacent to either the right or the left nostril, depending on the trail of the flexible conduit 18, to deliver a physiological acceptable does of NO to satisfactorily decrease pulmonary artery pressure.

In use, the administration of nitric oxide is at a continuous flow of the gas throughout the horse's respiratory cycle during exercise. The concentration of the gas delivered is dilutionally derived and therefore based on the individual's minute ventilation (or the quantity of air exchanged in a given minute). This minute ventilation parallels footspeed of the horse in meters/second, e.g. at 10 m/sec. $V_E$=approximately 1400 l/min. However, the estimation of footspeed in a training and/or competitive environment is rather subjective and hence concentration of the nitric oxide delivered is a function of arbitrary flow rates.

An exemplary source tank 12 of nitric oxide contains about $10^3$ ppm/$N_2$/N. For a minute ventilation concentration of 20 ppm nitric oxide, the horse needs to receive 2% of the tank concentration and therefore 2% of the subject's $V_E$, in this case about 28 l/min. Table 1 serves as a general outline.

TABLE 1

| Treadmill m/sec. | Subject's $V_E$ Liters/min. | Targets Nitric Oxide in ppm | Nitric Oxide Flow Rate Liters/min. |
|---|---|---|---|
| 0 | 157 ± 63 | 20 | 3.14 |
|   |          | 50 | 7.85 |
| 8 | 1300 | 20 | 26 |
|   |      | 50 | 25 |
| 10 | 1400 | 20 | 28 |
|    |      | 50 | 70 |
| 13 | 1700 | 20 | 34 |
|    |      | 50 | 85 |
| 0 | 65-95 | 20 | 65-1.3 |
|   |       | 50 | 3.25 |
|   |       |    | 95-1.9 |
|   |       |    | 4.75 |

The rationale for the continuous flow of nitric oxide is the assumed technical difficulty in gating the delivery of the gas to the inspiratory phase of the horse's respiratory cycle. Hence the aforementioned table served as a guide for implementing the administration of nitric oxide. In an ideal environment, the exact minute ventilation of the animal is known under varying intensities of exercise. The required flow/concentration (i.e. 20, 50 ppm of nitric oxide) is then easily calculated based on the minute ventilation.

It is contemplated by the scope of the present invention that improvements in nasal insufflation will be realized by, for example, gating the flow rate of the nitric oxide to a synchronous parameter of the animal such as heart rate. Synchronous insufflation is both advantageous and necessary in order to quantify the nitric oxide administration and minimize inadvertent human and/or mechanical error.

An alternative technique for the administration of nitric oxide to equine to prevent exercise induced pulmonary hemorrhaging is directed to the use of phosphodiesterase inhibitors. The family of compounds known as phosphodiesterase inhibitors are enzymes that prevent catalyzing hydrolysis of an ester linkage by a phosphodiesterase. More specifically, cGMP which is the effectual compound at the cellular level and is derived from nitric oxide, is normally degraded very rapidly in vivo by the action of endogenous phosphodiesterase. This necessitates a constant instantaneous supply of NO being maintained in order to accomplish the desire therapeutic effect. With the addition of a phosphodiesterase inhibitor coupled to nitric oxide, there is a muting of the degradation of cGMP, resulting in a prolonged efficacy at the target level. Phosphodiesterase inhibitor useful with the present invention include 1,4-dihydro-5-(2-propoxyphenol)-7H-1,2,3-triazolo-(4,5-d)-pyrimidine-7-one) commercially available under the designation ZAPRINAST, and NA 1-(-6-chloro-4-(3,4-methylenedioxybenzyl)aminoquinazolin-2-yl)-piperidine-4-carboxylate sesquihydrate, commercially available under the designation E4021.

The administration of nitric oxide and a phosphodiesterase inhibitor embraces the following methodology. Prior to the initiation of the equine program (training/racing), the candidate is administered NO via nasal insufflation at a fixed concentration (10 to 80 ppm) and flow rate (predicated on the horse's tidal volume/minute ventilation) for a period of time ranging from about 2 to 10 minutes. Shortly thereafter, the phosphodiesterase inhibitor is given intramuscularly in a stringently pre-formulated dosing regimen. A preferred dosage of the preferred phosphodiesterase inhibitors is about 0.01 mg/kg to 5 mg/kg. The NO gas is withdrawn and the protocol terminated. This venue obviates the need for continuous application of the nitric oxide during the equine's performance (training/racing) and facilitates the non-encumbrance of both the animal and the sophisticated techniques required with the employment of NO alone.

The following examples describe the manner and process of nasal insufflation of nitric oxide to an equine to reduce pulmonary artery pressure according to the present invention, and they set forth the best mode contemplated by the inventors of carrying out the invention, but they are not to be construed as limiting.

EXAMPLE

Three horses were studied at rest with measurement of baseline parameters i.e. right atrial (RA), right ventricular (RV), pulmonary artery (PA), and pulmonary artery wedge pressure (PAW) for a minimum of 15 minutes. Also quantified were pulmonary capillary pressure (Pcap) (0.5 of average mean of PA and PAW pressure). After completion of these measurements, gradations of exercise intensity began on a high speed treadmill. The horses walked for 1 minute at 2 m/sec. and continued in increments of 1 m/sec. in treadmill speed every minute until 6 m/sec was achieved. Subsequent increases to 8 m/sec. for 1 minute, 10 m/sec. for 2 minutes and 12 m/sec. for 2 minutes followed.

Immediately after completion of the 12 m/sec. treadmill exercise; catheter locations were confirmed and the microtip manometer signals checked against pressure signals from the fluid filled catheter. Data was collected 30 seconds to 1 minute prior to the end of each exercise level (i.e. 8, 10 and 12 m/sec.) Repeated measurements of RA, RV, PA, PAW and calculated Pcap were recorded. Following a rest period of 4 hours or more for each horse, the initiation of the nitric oxide protocol began.

The initial concentration of 20 ppm of nitric oxide began with the horse at the treadmill speed of 8 m/sec. followed by 10 m/sec. and 12 m/sec. Since the administration of nitric oxide is a constant flow system, the concentration of NO was dilutionally derived and therefore based on the animal's minute ventilation.

A second experimental run at 50 ppm was likewise employed. However, due in part to the necessity for maximizing the recovery of the horses, the experimental run of 50 ppm was performed on a separate day.

The results are listed in Table 2 at 20 ppm and 50 ppm of nitric oxide. All measurements are mm Hg, and calculated Pcap was recorded at thirty (30) seconds to one (1) minute prior to the end of each exercise level (i.e. 8 and 12 m/sec.).

TABLE 2

| 20 ppm nitric oxide inhalant | | | | |
|---|---|---|---|---|
| | 8 m/sec. | | 12 m/sec. | |
| | Before NO | After NO | Before NO | After NO |
| RA | 35–38 | 29–30 | 47–51 | 33–36 |
| PA | 95–98 | 78–80 | 112–115 | 90–95 |
| PAW | 42–46 | 30–33 | 57–59 | 40–45 |
| Pcap | 57–60 | 30–36 | 75–79 | 54–60 |

| 50 ppm nitric oxide inhalant | | | | |
|---|---|---|---|---|
| | 8 m/sec. | | 12 m/sec. | |
| | Before NO | After NO | Before NO | After NO |
| RA | 35–38 | 28–30 | 47–51 | 35–36 |
| PA | 95–98 | 78–81 | 112–115 | 89–96 |
| PAW | 42–46 | 32–33 | 57–60 | 40–45 |
| Pcap | 57–60 | 29–33 | 75–81 | 51–60 |

Results of these tests using nitric oxide as a selective pulmonary vasodilator have demonstrated a marked reduction in pulmonary vascular pressures and capillary stress failure/EIPH of greater than 30 percent by qualitative standards.

While the present invention has been particularly described in connection with certain specific embodiments thereof, it is to be understood that this is by way of illustration and not limitation, and the scope of the appended claims should be construed as broadly as the prior art will permit.

What is claimed is:

1. A method of preventing pulmonary hemorrhaging in equine during exercise, comprising the steps of:
   a) providing a breathable gas supply comprising nitric oxide at a concentration of about 10 ppm or greater;
   b) providing a nozzle means in fluid flow communication with the breathable gas supply and disposed proximate at least one of the horse's nares; and
   c) determining a physiological acceptable quantity of the breathable gas supply to be delivered into the horse's lungs from the nozzle means to prevent hemorrhaging during exercise by determining the horse's exercise minute ventilation and foot speed; and
   d) delivering the physiological acceptable quantity of the breathable gas supply into the horse's lungs from the nozzle means.

2. The method of claim 1 including continuously flowing the breathable gas throughout the entire duration of the exercise.

3. The method of claim 1 including regulating the flow rate of the nitric oxide to a synchronous parameter of the horses's heart rate.

4. The method of claim 1 including providing the breathable gas comprising the nitric oxide at a level of about 10 to 80 ppm.

5. The method of claim 1 including preventing hemorrhaging by reducing pulmonary vascular pressure in the horse.

6. A method of stimulating the production of cyclic 3',5'-monophosphate in the lungs of an a horse to prevent exercised induced pulmonary hemorrhaging during exercise, comprising the steps of:
   a) providing a breathable gas supply comprising nitric oxide at a concentration of about 10 ppm or greater;
   b) providing a nozzle means in fluid flow communication with the breathable gas supply and disposed proximate at least one of the horse's nares;
   c) exercising the horse; and
   d) determining a physiological acceptable quantity of the breathable gas supply to be delivered into the horse's lungs from the nozzle means by determining the horse's exercise minute ventilation and foot speed; and
   e) delivering the physiological acceptable quantity of the breathable gas supply into the horse's lungs from the nozzle means to stimulate cyclic 3',5'-monophosphate production throughout the duration of the exercise to thereby reduce pulmonary vascular resistance in the lungs to a degree sufficient to prevent hemorrhaging.

7. The method of claim 6 including continuously flowing the breathable gas throughout the duration of the exercise.

8. The method of claim 6 including regulating the flow rate of the nitric oxide to a synchronous parameter of the horse's heart rate.

9. The method of claim 6 including providing the breathable gas comprising the nitric oxide at a level of about 10 to 80 ppm.

10. The method of claim 6 including preventing hemorrhaging by reducing pulmonary vascular pressure in the horse.

11. A method of preventing exercised induced pulmonary hemorrhaging in equine, comprising the steps of:
   a) providing a breathable gas comprising nitric oxide at a concentration of about 10 ppm or greater;
   b) providing a nozzle means in fluid flow communication with the breathable gas and disposed proximate at least on of a horse's nares; and
   c) determining a physiological acceptable quantity of the breathable gas supply to be delivered into the horse's lungs from the nozzle means to prevent hemorrhaging during exercise by determining the horse's exercise minute ventilation and foot speed; and
   d) delivering the physiological acceptable quantity of breathable gas supply into the horse's lungs from the nozzle means for about 2 to 10 minutes on an anticipated duration and magnitude of exercise to which the horse is expected to be immediately subjected;
   e) intramuscularly administering a phosphodiesterase inhibitor to the horse;
   f) discontinuing the insufflation; and
   g) exercising the horse.

12. The method of claim 11 including selecting the phosphodiesterase inhibitor from the group 1,4-dihydro-5-(2-propoxyphenol)-7H-1,2,3-triazolo-(4,5-d)-pyrimidine-7-one) or NA 1-(-6-chloro-4-(3,4-methylenedioxybenzyl)-aminoquinazolin-2-yl)- piperidine-4-carboxylate sesquihydrate, and mixtures thereof.

13. The method of claim 11 including administering the phosphodiesterase inhibitor in a dosage of about 0.01 to 5 mg/kg.

14. The method of claim 11 including providing the breathable gas comprising the nitric oxide at a level of about 10 to 80 ppm.

15. The method of claim 11 including selecting the phosphodiesterase inhibitor from 1,4-dihydro-5-(2-propoxyphenol)-7H-1,2,3-triazolo-(4,5-d)-pyrimidine-7-one) or NA 1-(-6-chloro-4-(3,4-methylenedioxybenzyl)-aminoquinazolin-2-yl)-piperidine-4 carboxylate sesquihydrate, and mixtures thereof.

16. The method of claim 11 including preventing hemorrhaging by reducing pulmonary vascular pressure in the horse.

17. The method of claim 11 wherein the maximum foot speed is about 8 to about 13 meters/sec.

18. The method of claim 11 wherein the horse's predetermined minute ventilation is about 1300 to about 1700 liters/minute.

19. A method of stimulating the production of cyclic 3',5'-monophosphate in the lungs of an equine to prevent exercised induced pulmonary hemorrhaging, comprising the steps of:

a) providing a breathable gas comprising nitric oxide at a concentration of about 10 ppm or greater;

b) providing a nozzle means in fluid flow communication with the breathable gas and disposed proximate at least one of a horse's nares;

c) determining a physiological acceptable quantity of the breathable gas to be delivered into the horse's lungs from the nozzle means to prevent hemorrhaging during exercise by determining the horse's exercise minute ventilation and foot speed; and d) delivering the physiological acceptable quantity of the breathable gas into the horse's lungs from the nozzle means for about 2–10 minutes in a quantity sufficient to produce cyclic 3',5'-monophosphate at a quantity sufficient to prevent hemorrhaging based on the anticipated duration and magnitude of exercise to which the horse is expected to be immediately subjected;

e) intramuscularly administering a phosphodiesterase inhibitor to the horse in a quantity sufficient to mute the degradation of 3',5'-monophosphate throughout the anticipated duration of exercise;

f) discontinuing the insufflation; and g) exercising the horse.

20. The method of claim 19 including administering the phosphodiesterase inhibitor in a dosage of about 0.01 to 5 mg/kg.

21. The method of claim 19 including providing the breathable gas comprising the nitric oxide at a level of about 10 to 80 ppm.

22. The method of claim 19 including preventing hemorrhaging by reducing pulmonary vascular pressure in the horse.

23. The method of claim 19 wherein the maximum foot speed is about 8 to about 13 meters/sec.

24. The method of claim 19 wherein the horse's predetermined minute ventilation is about 1300 to about 1700 liters/minute.

25. An apparatus for preventing exercised induced pulmonary hemorrhaging in equine, which comprises:

a) container means adapted to be carried by a horse during exercise, wherein the container means holds a breathable gas comprising nitric oxide in a concentration of about 10 ppm or greater;

b) nozzle means in fluid flow communication with the container means, wherein the nozzle means is positionable proximate at least one nostril of a horse;

c) means including a flow meter for determining a physiological acceptable quantity of the breathable gas to be delivered into a horse's lungs from the nozzle means to prevent hemorrhaging during exercise and for determining a horse's exercise minute ventilation and foot speed;

d) means including the nozzle means for delivering the physiological acceptable quantity of the breathable gas into a horse's lungs to thereby reduce pulmonary vascular resistance in a horse's lungs to a degree sufficient to prevent hemorrhaging.

26. The apparatus of claim 25 further including a pressure regulator.

27. The apparatus of claim 25 wherein the breathable gas includes the nitric oxide at a concentration of about 10 to 80 ppm.

28. The apparatus of claim 25 wherein the physiological acceptable quantity of breathable gas reduces pulmonary vascular pressure in a horse.

* * * * *